United States Patent [19]

Greco

[11] 4,215,229
[45] Jul. 29, 1980

[54] PROCESS FOR ALKYLATING PHENOLIC COMPOUNDS TO PRODUCE ORTHO- AND PARA-MONOALKYLATED PHENOLS AND 2,4- AND 2,6-DIALKYLATED PHENOLS

[75] Inventor: Nicholas P. Greco, Pittsburgh, Pa.

[73] Assignee: Koppers Company, Inc., Pittsburgh, Pa.

[21] Appl. No.: 915,715

[22] Filed: Jun. 15, 1978

[51] Int. Cl.$^2$ ............................................. C07C 37/20
[52] U.S. Cl. ................................... 568/804; 568/780; 568/799
[58] Field of Search ............... 568/799, 780, 804, 789, 568/736

[56] References Cited

U.S. PATENT DOCUMENTS

| | | | |
|---|---|---|---|
| 2,194,215 | 3/1940 | Bruson et al. | 568/736 |
| 2,841,623 | 7/1958 | Norton et al. | 568/780 |
| 3,394,399 | 7/1968 | Bajer et al. | 568/799 |
| 3,461,722 | 8/1969 | Previc | 568/799 |
| 3,592,951 | 7/1971 | Zoweski | 568/780 |
| 3,919,332 | 11/1975 | Wollensak | 568/780 |
| 3,946,086 | 3/1976 | Gershanov et al. | 568/780 |

*Primary Examiner*—Werren B. Lone

*Attorney, Agent, or Firm*—Herbert J. Zeh, Jr.; Oscar B. Brumback; J. Timothy Keane

[57] ABSTRACT

Ortho- and para-monoalkylated phenols and 2,4- and 2,6-dialkylphenols can be produced from phenolic compounds in good yields. The phenolic compound is reacted with an aldehyde having one to ten carbon atoms and a secondary aliphatic amine having a basic dissociation constant, $pK_b$, of less than about 3.6 measured at 25° C. The reaction is conducted in the liquid phase with at least a stoichiometric amount of the phenolic compound, the aldehyde and the secondary amine, or with an excess of the phenolic compound with the stoichiometric amounts of the aldehyde and the secondary amine. The reaction is conducted at a temperature in the range of around 0° C. to about 25° C., and the reaction produces an aminoalkylated phenol. The aminoalkylated phenol is contacted with hydrogen in the presence of a metal catalyst at a temperature of about 120° C. to about 140° C. at a hydrogen pressure not greater than 150 psi to produce a mixture of ortho-monoalkylphenol, para-monoalkylphenol and 2,4- and 2,6-alkylphenol. These compounds are separated to produce ortho-monoalkylphenol, para-monoalkylphenol, 2,4-dialkylphenol and 2,6-dialkylphenol.

16 Claims, No Drawings

PROCESS FOR ALKYLATING PHENOLIC COMPOUNDS TO PRODUCE ORTHO- AND PARA-MONOALKYLATED PHENOLS AND 2,4- AND 2,6-DIALKYLATED PHENOLS

BACKGROUND OF THE INVENTION

This invention relates to a process for producing ortho- and para-monoalkylphenols and 2,4- and 2,6-dialkylphenols. More particularly, the invention relates to an alkylation process for phenols that have a replaceable hydrogen in the ortho- or para- position with an aldehyde and a secondary amine to form the aminoalkylated phenol that then is subjected to hydrogenolysis to produce ortho-monoalkylphenol, para-monoalkylphenol, 2,4-dialkylphenol and 2,6-dialkylphenol. Phenolic compounds with alkylated ortho- positions and/or para- positions are useful as various industrial materials. For example, paracresol, 4-methylphenol, is useful in fumigating compositions, dyestuffs, organic intermediate for anti-oxidants, resins, pharmaceuticals, dyes, and pigments; and ortho-cresol is useful as a disinfectant and organic intermediate.

The method of alkylating phenols that have an open ortho- or para- position with an aldehyde and secondary amine to form an alkyl aminophenol that is then cleaved by hydrogenolysis to produce alkylated phenols is well known in the art. An example is U.S. Pat. No. 2,194,215 (Bruson et al.) which teaches the methylation of phenolic compounds by condensing the phenolic compounds with at least one molecular equivalent each of formaldehyde and a strongly basic, non-aromatic secondary amine to form phenolic tertiary amines. The phenolic tertiary amine obtained is then subjected to hydrogenolysis, whereby the secondary amine is reformed and a new methylated phenolic compound is produced. The hydrogenolysis is performed in the presence of the hydrogenation catalyst, copper chromite, at a temperature above 100° C. and below 300° C., and preferably between 150° C. and 200° C. By this process phenol can be converted into ortho-cresol, para-cresol, 2,4-xylenol, 2,6-xylenol or 2,4,6-trimethylphenol or mixtures thereof, depending upon whether one, two or three moles each of formaldehyde and a secondary amine are employed for the condensation.

Many hydrogenation catalysts are known in the art. These catalysts can exist in natural state or in the oxidized state. In referring to the oxidized state of a hydrogenation catalyst, the art generally refers to the oxidized hydrogenating components of the catalyst which are generally selected from the Group VIII metals of the Periodic Table of the elements and include iron, cobalt, nickel, ruthenium, rhodium, palladium, osmium, iridium and platinum. It is also known that these catalysts can be used as hydrogenolysis catalysts for cleaving compounds. An example of the use of some of these catalysts as hydrogenolysis catalysts is given in U.S. Pat. No. 3,946,086 (Gershanov et al.) which teaches a method for producing 2,6-dialkyl and 2,6-diaralkyl substituted derivatives of para-cresol. In this method phenol is alkylated with an olefine having from four to twelve carbon atoms or with styrene at a temperature in the range of 50° C. to 150° C. in the presence of a catalyst, namely, aluminum, to produce 2,6-dialkylphenol or 2,6-diaralkylphenol. The 2,6-dialkylphenol or 2,6-diaralkylphenol resulting from the alkylation is treated with a mixture of formaldehyde and dimethylamine or with a reaction product thereof having the formula

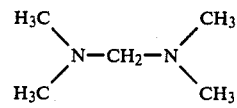

at a temperature of 20° C. to 100° C. to form N,N-dimethyl(3,5-dialkyl-4-hydroxybenzyl)/amine or N,N-dimethyl(2,5-diaralkyl-4-hydroxybenzyl)/amine. These tertiary amines are subsequently subjected to catalytic hydrogenolysis with either pure hydrogen or a hydrogen-containing gas, such as a methane-hydrogen mixture or a nitrogen-hydrogen mixture. The hydrogenolysis catalysts useful in this teaching are those that are conventionally used for this process, such as nickel, palladium, platinum, and copper. The teaching suggests that it proves most expedient to use a nickel-chromium catalyst, nickel-copper catalyst, and especially, alloyed nickel-aluminum-titanium catalyst. Also, the amination should be carried out in the medium of a saturated aliphatic alcohol such as monobasic aliphatic alcohols having one to four carbon atoms. The amination step must lead to the positioning of the alkyl groups in the para- position since the ortho- position is already occupied in the starting material. The products produced from the process of this teaching are the 2,6-dialkyl and 2,6-diaralkyl substitute derivates of para-cresol.

One skilled in the art is not taught by the aforementioned teachings on how to produce para-monoalkylated phenol or para-cresol in good yield and purity from a phenolic compound containing an open ortho- or para- position.

SUMMARY OF THE INVENTION

In accordance with the present invention, there has been discovered a process for producing ortho- and para-monoalkylphenols and 2,4- and 2,6-dialkylphenols and especially para-substituted monoalkylated phenols in good yield and of high purity from phenolic compounds containing an open ortho- or para- position.

The present invention comprises reacting a phenolic compound that has a replaceable hydrogen in at least the para- position or in the para- position and one or more ortho- positions, and a secondary amine having a basic dissociation constant, $pK_b$, of less than around 3.6 measured at 25° C., and an aldehyde having one to ten carbon atoms where the secondary amine and the aldehyde are in stoichiometric quantities and the phenolic compound is in a stoichiometric quantity or in excess of stoichiometric quantities. The reaction occurs in the liquid phase at a temperature in the range of around 0° C. to around 20° C. and an aminoalkylated phenolic compound is produced. Then the aminoalkylated phenolic compound is contacted with hydrogen at a pressure no higher than around 150 psi and at a temperature in the range of about 120° C. to about 140° C. in a glass-lined vessel in the presence of a catalyst containing palladium, platinum, iridium, rhodium or rubidium to produce a mixture containing predominantly para-monoalkylphenol with smaller amounts of ortho-monoalkyl-phenol and 2,6- and 2,4-dialkylphenol. The para-monoalkylphenol is separated from the mixture to produce the para-alkylphenol in a good yield and of high purity.

DETAILED DESCRIPTION OF THE INVENTION

The phenolic compounds that are useful in the process of this invention are those that contain a replaceable hydrogen in at least the para- position and in one or both of the ortho- positions, and is expressed by the following general formula:

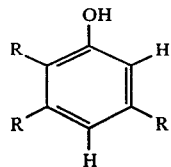

wherein each R independently represents a monovalent substituent such as a hydrogen atom, an alkyl group containing one to six carbon atoms, an aryl group or an aralkyl group. In the formula the availabe ortho-hydrogen can be at either ortho- position 2 or 6, or at both othro- positions. Specific examples of the phenolic compound used in the process of the present invention include phenol, meta-cresol, ortho-cresol, 2,3-xylenol, 2,5-xylenols, phenols having substituted thereon one or more alkyl radical groups, such as: ethyl, propyl, isopropyl, butyl, amyl, hexyl, cyclohexyl, heptyl, heptyl, octyl, nonyl, decyl, and the like in one of the ortho positions on the ring and/or in the meta positions on the aromatic ring. Also included are fused ring phenols such as naphthols and similar compounds, as well as polyhydric phenols exemplified by resorcinol, pyrogallol and hydroquinone.

The alkylating compounds of the present invention are aldehydes having one to ten carbon atoms. Examples of the aldehydes include formaldehyde in aqueous form or in polymeric form, acetaldehyde, propionaldehyde, isopropionaldehyde, n-butyraldehyde, isobutyraldehyde, sec-butyraldehyde, tert-butyraldehyde. Also similar compounds like pentanal, hexanal, heptanal, octanal, nonal, and decal and other compounds such as 2-methylpentanal, 3,-methylpentanal and 4-methylpentanal. The preferred aldehyde for use in the present invention is formaldehyde, and it is preferred that the formaldehyde be in the form of paraformaldehyde in order to maximize the yield of para-monoalkylphenol, which would be para-cresol.

The secondary amine used in the process of this invention must have sufficient basicity to form the aminoalkylphenol upon reaction with the phenolic compound and the aldehyde. The secondary amine must have a basic dissociation constant, $pK_b$, less than around 3.6 measured at 25° C. Secondary amines which may be used include: diethylamine, dimethylamine, diisopropylamine, diisobutylamine, piperidine, and dibutylamine. Such secondary amines are chosen as a function of their pK, a list of which, for example, is given in the "Handbook of Chemistry and Physics," 53rd Edition 1972–73 by Robert C. Weast, Part D, Page 117. The use of a readily available secondary amine such as dimethylamine, diethylamine, diisopropylamine and piperidine is particularly recommended.

The hydrogenation catalyst used in the process of the present invention in the hydrogenolysis step, where the aminoalkylphenol is cleaved into alkylphenols and the secondary amine, contains the noble metals selected from the group consisting of iridium, palladium, platinum, rhodium and rubidium and mixtures thereof. The metallic components may or may not be deposited on a support, but are generally deposited on an inorganic oxide base or carrier material. Suitable carrier materials are silica aluminas, the crystalline aluminosilicates, alumina, porous or nonporous carbon blacks of small or large specific surface areas, and other carbonaceous materials such as activated carbon, coke, or charcoal and other supporting material like thoria, or kieselguhr. Commercial activated carbons which may be used are available under the trade names of Norrit, Nuchar, Darco, but other similar carbon materials familiar to those skilled in the art may be used. The hydrogenolysis catalyst may be prepared by any conventional method, when used without a support and when used with a support; it may be prepared by any conventional method for impregnating a porous carrier with a metallic component. One such manner is to make a composite of the metal component with the catalyst base by forming an aqueous solution of the halide of the metal such as platinum chloride, palladium chloride, etc., further diluting the solution and adding the resultant diluted solution to the base in a steam dryer. Other suitable metal solutions may be employed such as colloidal solutions or suspensions, including the desirable metal cyanides, metal hydroxides, metal oxides, and metal sulfides, etc. In cases where these solutions are not soluble in water at temperatures used, other suitable solvents such as alcohols, ethers, etc. may be utilized.

In the process of this invention, the reactions involved are the following:

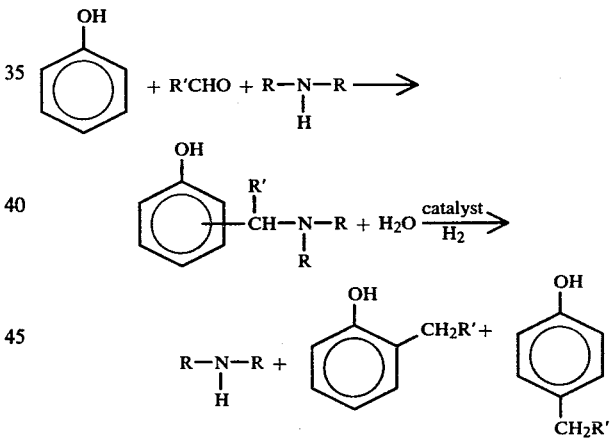

The phenolic compound is mixed with the secondary amine and the aldehyde is added to this mixture, and these compounds are reacted to produce the aminoalkylphenol. This reaction can take place in any vessel known to those skilled in the art for conducting chemical reactions. The suitable mole ratio of the phenolic compound, secondary amine, and aldehyde fed to the reaction vessel is such that the aldehyde and secondary amine are in stoichiometric quantities and the phenolic compound is in excess of the stoichiometric quantity. This reaction is conducted at a temperature in the range of around 0° C. to around 20° C., but lower temperatures can be used, resulting in a slower and undesirable reaction rate. Elevated temperatures above room temperature are not desirable since they do not favor the formation of the para-substituted alkylphenol. The reaction is also conducted in the liquid phase and may be conducted in the presence of a solvent. Suitable solvents for use in the process of the invention are lower alkyl alcohols such as methanol, ethanol, propanol, isopropanol, butanol and sec-, iso-, and tert-butanols. The reaction is best carried out until a maximum quantity of the aminoalkylated phenol is produced, but shorter times may be used although such use would not be desirable from an economic standpoint.

After the water is stripped from the solution or after a sufficient amount of methanol is added to make the mixture of water and aminoalkylated phenol and unreacted reactants a homogeneous mixture and act as a solvent, in order to prevent the water from adversely affecting the catalyst, the aminoalkylated phenol is then subjected to hydrogenolysis by contacting the aminoalkylated phenol with hydrogen. The contacting occurs at a hydrogen pressure no higher than 150 psi and at a temperature in the range of about 120° C. to about 140° C. in the presence of a noble metal catalyst selected from iridium, palladium, platinum, rhodium, or rubidium, or mixtures thereof. The hydrogenolysis is carried out in a glass-lined vessel to prevent any metals other than the type present in the catalyst from contacting the reactants. The hydrogenolysis cleaves the aminoalkylated phenol to produce a mixture of alkylated phenols containing predominantly the para-alkylated phenol with smaller quantities of the ortho-alkylated phenol and still smaller quantities of the 2,4- and 2,6-dialkylated phenol. Also produced is the secondary amine used in the reaction with the phenolic compound and the aldehyde. This secondary amine can be recycled to the reaction vessel where the phenolic compound, secondary amine and aldehyde are reacted. Also, the hydrogenolysis catalyst can be removed from the glass-lined reaction vessel, filtered and recycled for reuse in the glass-lined reaction vessel for further hydrogenolysis.

The alkylated phenolic mixture containing predominantly the para-alkylated phenol after the secondary amine has been removed from the mixture for recycling is treated to a separation step to produce the para-alkylated phenol in a good yield and of a high purity. In the process of the present invention, the alkylated phenolic compounds can be separated from the mixture containing the alkylated phenolic compounds and the secondary amine and the catalyst by any method known to those skilled in the art. This separation step usually includes springing the phenolics from the mixture by acidifying the mixture and extracting the alkylated phenolic compounds. The alkylated phenolic compounds are then distilled to produce predominantly the para-alkylated phenol along with minor amounts of ortho-alkylated phenol and 2,4- and 2,6-dialkylphenols.

In the process of the present invention it is believed, but the invention is not limited by this belief, that the lower temperatures and the stoichiometric amount and especially the excess amount of the phenolic compound in the reaction between the phenolic compound, the secondary amine and the aldehyde influences the basic reaction so that the aminoalkylated phenol that is produced is predominantly alkylated in the para- position. In the catalytic hydrogenolysis step it is believed that the noble metals iridium, palladium, platinum, rhodium and rubidium work so well because they do not form chelates with the aminoalkylated phenol, as do such catalysts as nickel and copper chromite. Also, the use of the glass-lined reaction vessel in the catalytic hydrogenolysis step prevents the presence of metallic components other than those present in the hydrogenolysis catalyst from adversely affecting the catalytic hydrogenolysis reaction, while also preventing corrosion of the reaction vessel.

The process of the present invention is particularly applicable to the alkylation of phenol to produce para-cresol. In this application, phenol, monohydroxybenzene, is contacted with a secondary amine, preferably diethylamine, and with formaldehyde, preferably paraformaldehyde, in an amount such that diethylamine and paraformaldehyde are in stoichiometric quantities and the phenol is in a quantity in excess of stoichiometric. Preferably, the quantities of the reactants are around two moles of phenol to around one mole of diethylamine and around one mole of paraformaldehyde. Preferably, the order of addition of the reactants is to add the diethylamine to the phenol and then add the paraformaldehyde. The reactants are reacted in the liquid phase and methanol is used as the solvent for the reaction. The reaction occurs at a temperature in the range of around 0° C. to around 25° C., and preferably about 5° C. to about 15° C. The product of the reaction are aminomethylated phenols which are predominantly the 4-diethylaminomethylphenol and the smaller amount of 2-diethylaminomethylphenol, with minor quantities of 2,4- and 2,6-di(diethylaminomethyl)phenol, and also water. This mixture of aminomethylated phenols is contacted with hydrogen at a pressure no higher than around 150 psi, and preferably 20 to 40 psi, in a glass-lined vessel at a temperature in the range of about 120° C. to 140° C. in the presence of a palladium on carbon catalyst to produce a mixture of monomethylated phenols, the secondary amine, and a small quantity of dimethylated phenols. The mixture contains predominantly para-cresol, with a smaller amount of ortho-cresol; the secondary amine, diethylamine; and a smaller quantity of 2,4- and 2,6-xylenol.

In separating the product mixture into para-cresol, ortho-cresol and dimethylated phenols and recovering the diethylamine, this separation can be performed by any method known to those skilled in the art for separating these compounds. Preferably, the product mixture containing the predominant amount of para-cresol with smaller amounts of ortho-cresol and xylenols is separated by the following prodecure. The product mixture is subjected to filtration to remove the palladium on carbon catalyst from the alkylated mixture. Then the methanol and around 50 percent of the diethylamine is distilled from the filtrate of the product mixture leaving behind a mixture of cresols and any unreacted phenol and diethylamine salts of the phenols and cresols. To this mixture there is added an acid, which can be any acid known to those skilled in the art, but is preferably dilute sulfuric acid for economic reasons, which springs the phenolic compounds from the mixture and produces an organic fraction containing a phenolic compound, and an aqueous fraction containing salts of the amine and the sulfuric acid. These fractions are separated by extraction with ether so that the ether fraction containing the phenolic compound is distilled to produce the para-cresol product, while also producing smaller amounts of an ortho-cresol product and still smaller amounts of 2,4- and 2,6-xylenol. The aqueous fraction which contains the salts of the amine and sulfuric acid is treated with caustic and distilled to produce the amine, diethylamine, which is then recycled to the amino alkylation step.

The amount of catalyst used in the hydrogenolysis step is generally between about 0.001 and about 1 percent of the weight of the amino derivatives employed in the reaction. This quantity of palladium is preferentially between about 0.01 and about 0.1 percent by weight of the amino derivatives.

The foregoing process may be carried out as a batch-type, semi-continuous or continuous operation utilizing a fixed or moving bed catalyst system for the aminoalkylation step if a catalyst is used and for the hydrogenolysis step. One embodiment entails the use of a fluidized catalyst zone for a hydrogenolysis step, where, in the glass-lined vessel, the mixture of aminomethylated phenols is passed countercurrently or co-currently through a moving fluidized bed of the palladium on carbon catalyst. The fluidized catalyst, after use, is filtered from the product mixture and is conducted or recycled to the glass-lined vessel for reuse. After the palladium on carbon catalyst has been used for a period of time, it may require regeneration, which can be performed by any method known to those skilled in the art.

The invention is more concretely described with reference to the examples below wherein all parts and percentages are by weight unless otherwise specified. It is emphasized that the examples are intended to illustrate the present invention and not to limit it. Example 1 shows an illustrative example of the use of a hydrogenolysis catalyst other than those employed in the present invention where this use fails to produce the desired products. Example 2 shows an illustrative example of the use of a noble metal catalyst of the type specified in the invention, but where the hydrogenolysis step of the process is performed in a stainless steel reactor and not a glass-lined reactor. The remaining examples depict specific compounds, temperatures and procedures used in the process of the invention.

ILLUSTRATIVE EXAMPLE 1

Phenol (94 grams, 1 mole) piperidine (75 grams, 0.9 mole) was stirred at room temperature and 40 grams of aqueous formaldehyde (0.50 mole) as a 38 percent solution was added dropwise at 25° C. to 35° C. After the addition, the mixture was stirred an additional hour and then it was heated to 90° C. for one (1) hour. Water and any unreacted piperidine was distilled off under vacuum. To the distillation residue there was added more phenol (110 grams) and copper chromite catalyst (10 grams), and the residue with catalyst was charged to a glass liner inserted in a 2.5 liter stainless steel reactor. Hydrogen was pressured into the vessel and the reaction mixture of residue, catalyst and hydrogen was stirred at 220° C. Only one-half the theoretical hydrogen was consumed. The product, after the catalyst was removed by filtering, was distilled. The distillation gave a 33 percent yield of para-cresol and a 2 percent yield of ortho-cresol with a large amount of a non-distillable residue.

Although the ratio of para-cresol to ortho-cresol was good, the yield of para-cresol was poor. It is believed the ratio was high because the ortho aminomethyl product of phenol from the amination step reacted with the catalyst and did not produce ortho-cresol on hydrogenolysis. It is believed the yield was poor since some of the reactants reacted with the catalyst. Also, 2,4- xylenol was not found in the product, which is another example of the ortho-substituted aminomethylation product reacting or chelating with the catalyst.

ILLUSTRATIVE EXAMPLE 2

Phenol (47 grams, 0.5 mole), piperidine (70 ml) were mixed and formaldehyde (40 grams of 38 percent aqueous solution, 0.5 mole) was added dropwise at a temperature of 20° C. to 25° C. The mixture was stirred for one (1) hour after addition and heated on a steam cone for another hour. After standing overnight at room temperature, unreacted piperidine, water and formaldehyde were distilled off at reduced pressure. The product remaining after the distillation was transferred to an American Instrument 300 ml stainless steel shaker autoclave, and one (1) gram of 5 percent platinum on carbon catalyst was added to the vessel. In addition, hydrogen was metered into the autoclave at 1500 psig and 150° C. This is the lowest temperature at which the aminomethylation product of phenol would hydrogenate. The product was placed in benzene, and after filtering the catalyst, the product was distilled at ordinary pressure. After distilling off the benzene, 70 grams of product and 31 grams of a non-distillable residue were obtained. The product contained, from gas chromatographic analysis, 13.7 percent ortho-cresol, 27 percent phenol and 19.6 percent para-cresol, and the remainder of the product was unidentified. The distillation residue was analyzed for metals by atomic absorption and it was found that the residue contained: 23 ppm of chromium, 375 ppm of iron, and 1060 ppm of nickel. All of these metals are components of the stainless steel reactor vessel.

Even though a nobel metal hydrogenation catalyst as specified in the invention was used, the reactants reacted with the walls of the stainless steel reactor. These reactions lead to a product with a poor yield and a poor ratio of para-cresol to ortho-cresol in the product. Also, these reactions caused the walls of the reactor not protected by a glass lining to have pits and other corrosion marks.

ILLUSTRATIVE EXAMPLE 3

Phenol (94 grams, 1.0 moles) and dimethylamine (180 grams of 25% aqueous solution, 1.0 moles) were heated with agitation to 60° C. while paraformaldehyde (30 grams, 1.0 moles) was added in portions. As the paraformaldehyde dissolved, the heat of reaction served to maintain the reaction temperature at 60° to 65° C. without any external heating. After all of the paraformaldehyde was added, the mixture was heated on a steam bath at 90° C. for an additional two (2) hours. Finally the reaction mixture was dehydrated by distillation under vacuum on a steam bath at 50° C. and a pressure of 45 millimeters mercury which gave 138 grams (92% yield) of the mannich base, amino methylated phenol. The steam distillate was extracted with ether to give an additional ten grams (7% yield) of the reaction product.

The aminomethylated phenol (138 grams, 0.92 mole) was charged to a glass liner, inserted in the shaker autoclave and hydrogenated in the presence of one gram of 5 percent palladium on carbon catalyst at 180° C. under 170 psig of hydrogen until hydrogen absorption ceased after one hour. The product was filtered and the filtrate was flash-distilled on the steam bath at 9° C. and 10 millimeters mercury pressure to a dry pot. The distillate was heated to 180° C. at atmospheric pressure to flash off dimethylamine and the residue, 101.5 grams, was analyzed by gas chromatography (weight percent). The yields of the product were as follows: phenol 7.6 percent, ortho-cresol 34 percent, para-cresol 17 percent, 2,6-xylenol 9 percent, 2,4-xylenol 23 percent, and 2,4,6-trimethylphenol 6 percent.

This example shows the production of a product with a low ratio of para-cresol to ortho-cresol due to the higher temperatures used in the amination step.

ILLUSTRATIVE EXAMPLE 4

Phenol (94 grams, 1.0 moles) and dimethylamine (180 grams of 25% aqueous solution, 1.0 moles) were stirred together and maintained at 25° C. while formalin (82.2 grams of 36.9% aqueous formaldehyde, 1.0 moles) was added. After the addition, the nearly homogeneous reaction mixture was heated at 90° C. for one hour. The reaction mixture was dried by distilling over water on a steam bath at 50° C. and 45 millimeters of mercury pressure to leave 143 grams of the aminomethylated phenol (151 grams theoretical). The aqueous distillate was extracted with ether and gave an additional 8 grams of reaction product.

The aminomethylated phenol was hydrogenated in 4.5 hours in the presence of 1 gram of 5 percent palladium on carbon catalyst under the same conditions as those in Example 5. Flash distillation of the filtered hydrogenated product at 110° C. and a pressure of 10 millimeters of mercury to a dry pot and redistillation at atmospheric pressure drove off dimethylamine and gave 98 grams of a water-white distillate. By gas chromatographic analysis, the conversion of phenol was 65 percent, and on a phenol-free basis, the following yields of products were obtained: 54 percent ortho-cresol, 29 percent para-cresol, 11 percent 2,4-xylenol, and 0.5 percent, 2,6-xylenol.

This example shows that when equimolar or stoichiometric amounts of the reactants, phenol, dimethylamine and formaldehyde are used, the product does not contain the maximum high ratio of para-cresol to ortho-cresol possible when an excess stoichiometric amount of phenol is used.

EXAMPLE 5

A mixture of phenol (94 grams, 1.0 moles), piperidine (43 grams, 0.5 mole), and methanol (50 moles) was cooled to 10° C. with agitation. Paraformaldehyde (15 grams, 0.5 mole) was added all at one time and the reaction temperature was maintained at 10° to 13° C. for 1.5 hours. The temperature was then allowed to rise to 25° C. The reaction mixture was heated to 85° C. and hydrogenated in a glass-lined autoclave in the presence of 1 gram of 5 percent palladium on carbon catalyst at a temperature of 120° to 130° C. for two hours at 120–150 psig of hydrogen. The product was filtered and the methanol in the filtrate removed by distillation. This left a product weighing 154 grams which, on analysis by gas chromatography (weight percent), contained the following: 37.5 percent phenol, 11.1 percent ortho-cresol, 14.6 percent para-cresol, and 0.7 percent 2,4-xylenol. This corresponds to yields of 40.6 percent for ortho-cresol, 53.3 percent for para-cresol, and 2.3 percent for 2,4-xylenol based on the phenol consumed.

EXAMPLE 6

Three runs were made using phenol and formaldehyde either in the form of paraformaldehyde or an aqueous solution wherein the mole ratio of the phenol to the formaldehyde was 2 to 1. These runs were conducted in a similar manner to that of Example 5, except were changes are indicated in the following table. Table 1 indicates the reactants used, the temperature of aminomethylation, cresol ratio, and mole percent yield of hydrogenated products.

Table I

PREPARATION OF PARA-CRESOL

| Run | Phenolic Compound | Amino Methylation in presence of Methanol (Temp. °C.) | Aldehyde | Amine | Cresol Ratio P-/O-Isomer | Mole Percent Yield of Products after Hydrogenation[1] | | | |
|---|---|---|---|---|---|---|---|---|---|
| | | | | | | Ortho-cresol | Para-cresol | 2,6-Xylenol | 2,4-Xylenol |
| 1 | Phenol | 10 to 13 | Paraformaldehyde | Piperidine | 1.5 | 35 | 52 | 0 | 5 |
| 2 | Phenol | 5 | 37% Aqueous formaldehyde | Piperidine | 1.1 | 39 | 43 | 0.5 | 5 |
| 3 | Phenol | 5 | Paraformaldehyde | Dimethylamine | 1.6 | 25 | 41 | 0 | 5 |

Footnote[1]
Based on the assumption of one mole of phenol consumed.

The foregoing has described a process for producing ortho- and paramonoalkylphenols and 2,4- and 2,6-dialkylphenols are especially para-substituded monoalkylated phenols in good yields and high purity from phenolic compounds containing an available hydrogen in at least the para position and/or ortho position. This process enables the use of monohydroxybenzene as a starting material to produce para-alkylated phenols in a fascile manner in good yield and with high purity.

I claim:

1. Process for alkylating phenolic compounds having an available hydrogen in at least the para position to produce a mixture containing predominantly para-monoalkylated phenols with a smaller quantity of ortho-monoalkylated phenols and dialkylphenols, comprising:

(a) reacting the phenolic compound with a saturated aliphatic aldehyde having one to about ten carbon atoms and a secondary amine having one to about ten carbon atoms and having a basic dissociation constant of less than around 3.6, wherein the amount of the aldehyde and the secondary amine are in stoichiometric amounts and the amount of the phenolic compound is in a stoichiometric or excess of the stoichiometric amount, and in the liquid phase and at a temperature in the range of around 0° C. to around 20° C. to produce a mannich base type aminoalkylated phenol;

(b) contacting the mannich base type aminoalkylated phenol with hydrogen at a pressure no higher than around 150 psig in a glass-lined vessel at a temperature in the range of about 120° to about 140° C. in the presence of a noble metal catalyst selected from the group consisting of palladium, platinum, rubidium, rhodium and iridium or a mixture thereof to produce a mixture containing predominantly para-monoalkylated phenol, with smaller amounts of ortho-monoalkylated phenol and dialkylated phenols and the secondary amine;

(c) separating the secondary amine from the mixture to produce a mixture containing predominantly para-monoalkylated phenol with smaller amounts of ortho-monoalkylated phenol and dialkylated phenols.

2. The process according to claim 1 wherein the separated secondary amine is recycled to be reacted with the phenolic compound and aldehyde.

3. Process according to claim 1 wherein the mixture of predominantly para-monoalkylated phenol with smaller amounts of ortho-monoalkylated phenol and dialkylated phenols is distilled to produce a para-monoalkylated phenol product and an ortho-monoalkylated phenol product and a dialkylated phenol product.

4. Process according to claim 1 wherein the noble metal catalysts are supported on materials selected from the group consisting of porous or non-porous carbon blacks, or silica.

5. Process according to claim 1 wherein the catalyst is filtered from the reaction product and recycled to the hydrogenolysis reaction.

6. Process according to claim 1 wherein the secondary amine is added to the phenolic compound before the aldehyde is added.

7. Process according to claim 1 wherein the reacting of the phenolic compound with the amine and the aldehyde is performed in methanol.

8. Process according to claim 1 wherein the catalyst used for the hydrogenation is a palladium on carbon catalyst.

9. Process for methylating phenol to produce a mixture containing predominantly para-cresol with smaller amounts of ortho-cresol and 2,4- and 2,6-xylenol in a good yield and high purity, comprising:

(a) reacting phenol and diethylamine and formaldehyde in quantities such that the diethylamine and formaldehyde are in stoichiometric quantities whereas the phenol is in an excess of the stoichiometric quantity in the liquid phase wherein methanol is present as a solvent at a temperature in the range of around 5° C. to about 15° C. to produce a mixture of mannich base type aminomethylated phenols;

(b) contacting the mixture of mannich base type aminomethylated phenols with hydrogen at a pressure no higher than around 150 psig and at a temperature in the range of about 120° to 140° C. in a glass-lined vessel in the presence of a palladium on carbon catalyst to produce a mixture containing predominantly para-cresol along with ortho-cresol, and 2,4- and 2,6-xylenol and the diethylamine;

(c) separating the diethylamine from the mixture to produce a mixture containing predominantly para-cresol along with ortho-cresol and 2,4- and 2,6-xylenol.

10. Process according to claim 9 wherein the formaldehyde used is a 37 percent aqueous formaldehyde solution.

11. Process according to claim 9 wherein the formaldehyde used is paraformaldehyde.

12. Process according to claim 9 wherein the diethylamine is separated from the mixture by contacting the mixture with an acid and then extracting the phenolic compounds with ether.

13. Process according to claim 9 wherein the separated diethylamine is recycled to the reaction of the phenol, secondary amine and formaldehyde.

14. Process according to claim 12 wherein the mixture in ether is distilled to produce para-cresol, ortho-cresol and 2,4- and 2,6-xylenol.

15. Process according to claim 11 wherein the diethylamine present in aqueous acid solution is made alkaline to release the diethylamine for recycle to the reaction of the phenol formaldehyde and diethylamine.

16. Process according to claim 1 wherein the secondary amine is selected from the group of dimethylamine or diethylamine.

* * * * *